United States Patent [19]

Linder

[11] Patent Number: 4,655,214

[45] Date of Patent: Apr. 7, 1987

[54] INFLATABLE INTRODUCER FOR AIDING THE INTUBATION OF CATHETERS AND ENDOTRACHEAL TUBES

[76] Inventor: Gerald S. Linder, P.O. Box 1085, Pacific Palisades, Calif. 90272

[21] Appl. No.: 624,487

[22] Filed: Jun. 28, 1984

[51] Int. Cl.$^4$ .................... A61M 25/00; A61M 16/00
[52] U.S. Cl. .................... 128/207.18; 128/207.14; 604/165; 604/167; 604/170
[58] Field of Search .................... 128/200.26, 207.14, 128/207.15, 344, DIG. 911, 207.18; 604/164, 165, 167, 170

[56] References Cited

U.S. PATENT DOCUMENTS

| | | | |
|---|---|---|---|
| 3,049,125 | 8/1962 | Kriwkowitsch | 128/344 |
| 3,087,493 | 4/1963 | Schossow | 128/207.15 |
| 3,766,924 | 10/1973 | Pidgeon | 128/344 |
| 4,198,981 | 4/1980 | Sinnreich | 128/344 |
| 4,219,026 | 8/1980 | Layton | 128/344 |
| 4,248,234 | 2/1981 | Assenza et al. | 604/170 |
| 4,261,339 | 4/1981 | Hanson et al. | 128/344 |
| 4,351,330 | 9/1982 | Scarberry | 128/207.15 |
| 4,471,779 | 9/1984 | Antoshkiw et al. | 128/344 |
| 4,502,482 | 3/1985 | DeLuccia | 604/165 |

FOREIGN PATENT DOCUMENTS 2928635 2/1981 Fed. Rep. of Germany .................... 128/207.14

Primary Examiner—Henry J. Recla
Attorney, Agent, or Firm—B. F. Spencer

[57] ABSTRACT

A soft, inflatable introducer, having a closed, rounded, distal-tipped sheath, is disclosed for insertion into the open proximal end of and through a hollow, cylindrical catheter. The closed, rounded, distal-tipped sheath protrudes partway beyond the open distal end of the catheter. The introducer includes a long, hollow, pliable tube having an open proximal end and having a distal end portion enclosed by the round, distal-tipped sheath. After insertion and placement of the introducer with sheath adjacent the distal end of the catheter, the sheath is inflated by applying air under pressure to the open proximal end of the hollow, pliable tube. A clamp or valve means closes and seals the proximal end of the hollow, pliable tube to maintain the sheath in its expanded, inflated condition while the catheter is being intubated. The inflated sheath, protruding partway beyond the distal end of the catheter, enhances the ease with which the catheter may be intubated into the passageway of a patient. After the catheter has been intubated, the clamp or valve means is opened to deflate the sheath, and the introducer is withdrawn.

2 Claims, 6 Drawing Figures

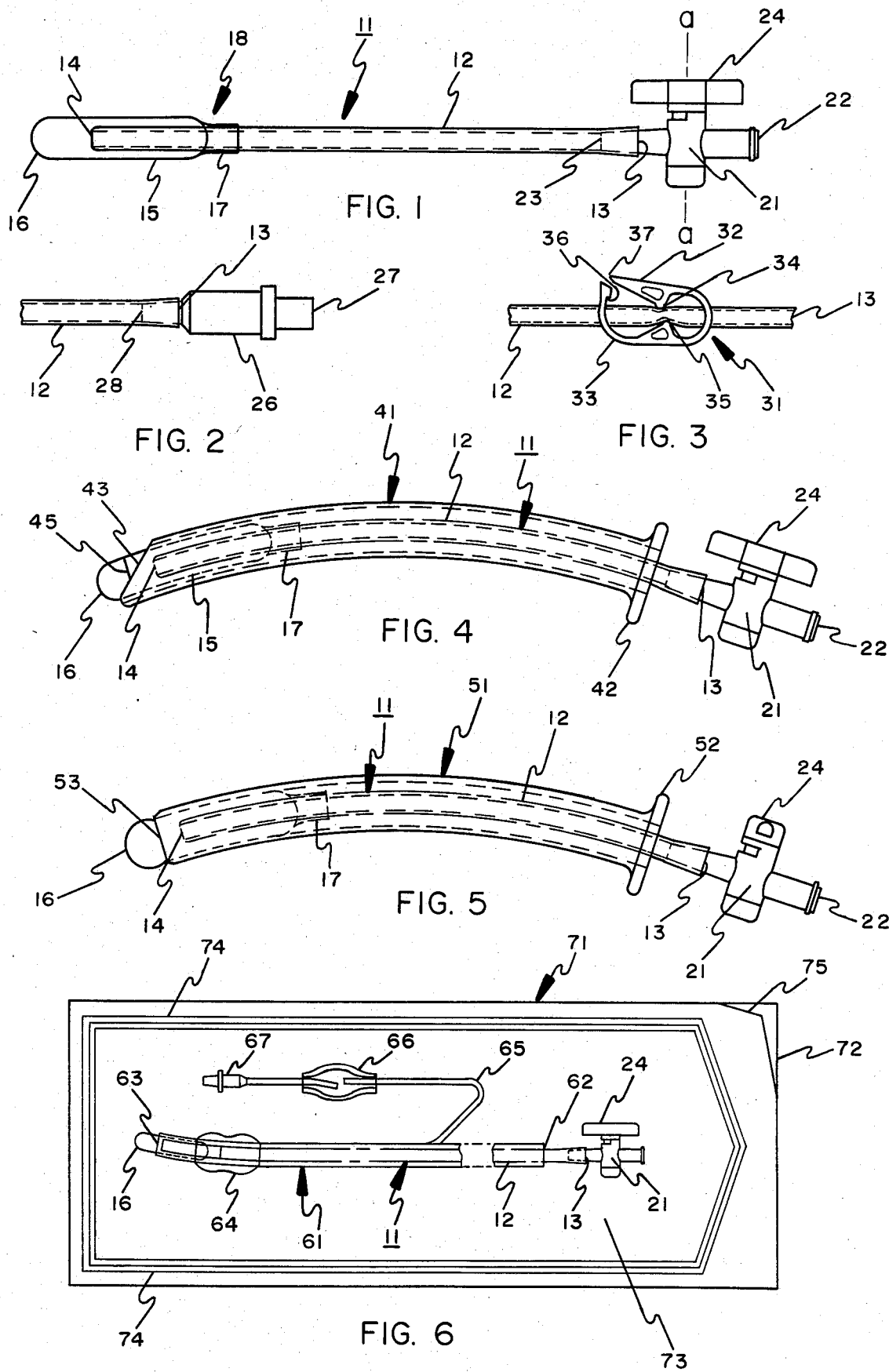

INFLATABLE INTRODUCER FOR AIDING THE INTUBATION OF CATHETERS AND ENDOTRACHEAL TUBES

BACKGROUND OF THE INVENTION

The present invention relates to an improved apparatus and method for the intubation of catheters, and, in particular, to a cylindrical, inflatable sheath having a closed, rounded tip that is inserted through the catheter and inflated adjacent the distal tip of the catheter prior to intubation, the cylindrical sheath being deflated and withdrawn following intubation.

A wide variety of catheters are available to the practising physician for intubation into the different passageways of a patient, as the need arises. Catheters vary in size, length, type and texture of material of which they are composed.

Of importance to the anesthesiologist is the class of catheter known in the art as endotracheal tubes designed for intubation into the trachea of a patient prior to anesthesia. Endotracheal tubes may be of the cuffed or uncuffed type, the uncuffed type being a smooth, long, hollow, pliable tube having open proximal and distal ends. The conventional cuffed endotracheal tube is provided with an inflatable cuff or balloon surrounding the outside distal end portion of the tube at a position above the distal tip. The ends of the cuff are secured to the outside wall of the tube to provide an airtight seal between the outside wall and the inside of the cuff. After intubation of a cuffed tube, the cuff is expanded by applying air under pressure to assure that the outside wall of the cuff embraces the trachea of the patient.

The distal tip or end of conventional catheters and endotracheal tubes is usually beveled at an angle which may vary between thirty to sixty degrees, depending, in part, upon the type of catheter to be used. In addition to the beveled distal tip, certain catheters and endotracheal tubes may have a small side or lateral opening through the side wall of the catheter at the distal end portion of the tube just above the beveled tip. This latter design is referred to in the art as a Murphy tip.

Intubation of the endotracheal tube, whether cuffed or uncuffed, may be accomplished either by inserting and passing the distal end portion through the patient's mouth and down into the trachea or, under certain conditions, by inserting and passing the distal end portion through the patient's nasal passageway past the pharynx and down into the trachea. In the former case, the endotracheal tube may be of a size and type identified as an oral, endotracheal tube. Endotracheal tubes, identified as either oral or nasal, may be intubated through the mouth or through the nose of the patient.

The intubation of catheters and endotracheal tubes is not without its problems. To aid the intubation of oral endotracheal tubes, the anesthesiologist may employ a catheter guide or stylette inserted within the endotracheal tube prior to intubation to enable the physician to shape the endotracheal tube, provide additional structural rigidity to the tube and afford an improved means for gripping and maneuvering the tube to accomplish intubation. My prior U.S. Pat. Nos. 3,957,055 and 4,185,639 pertain to improvements in the intubation of catheters and endotracheal tubes.

An additional type of catheter, of importance to the physician, is the nasal catheter designed to intubate the nasopharyngeal airway to insure that a patient may breathe satisfactorily when the condition of the patient's mouth prohibits oral intubation. The conventional nasal catheter is relatively short, is composed of highly flexible and pliable material, has a beveled, distal, open tip and a flared, open proximal end. Nasal catheters vary in size from six to eight and one-half millimeters. Due to the highly sensitive and delicate nature of the membranes of the nasopharyngeal airway, the intubation of nasal catheters and nasal endotracheal tubes has been known to cause trauma and injury to the patient. To minimize injury, the outer cylindrical surface of nasal catheters is textured, or frosted, and the surface lubricated to aid intubation. The wall thickness of the nasal catheter, generally, is less than that of endotracheal tubes, and the nasal catheter is pre-shaped, or curved, in an attempt to reduce injury and to aid intubation.

The present invention is directed to improvements in the intubation of catheters and endotracheal tubes, and especially to the intubation of nasal-type catheters. A soft, inflatable introducer, having a closed, rounded, distal-tipped sheath, is inserted into the open proximal end of and through a hollow, cylindrical catheter or endotracheal tube, with the distal-tipped sheath protruding partway beyond the open distal end of the catheter. The distal-tipped sheath is inflated, prior to intubation, to a diameter equal to or slightly larger than the outer diameter of the catheter. Both catheter and introducer are intubated into and through the passageway of the patient. The inflated sheath serves not only as a guide but also as a soft and flexible opener or enlarger of the sensitive membranes within the passageway, thereby enabling the catheter to penetrate and negotiate the varied shapes, obstacles or bends encountered. After the catheter has been successfully intubated within the passageway, the distal-tipped sheath is deflated and the introducer is withdrawn.

Accordingly, a principal object of the present invention is to provide an improved method and apparatus for the intubation of catheters which reduce trauma and injury to the patient.

Another object is to provide a soft, closed, inflatable sheath that may be placed ahead of the open distal tip of a catheter to guide the catheter into the passageway of a patient during intubation.

Still another object is to provide an improved catheter and inflatable introducer combination which enables the physician to more readily intubate the catheter, after which the introducer is deflated and removed.

An important object is to provide an improved procedure for the intubation of nasal catheters and endotracheal tubes into the nasopharyngeal airway of a patient.

The above objects of and the brief introduction to the present invention will be more fully understood, and further objects and advantages will become apparent, from a study of the following detailed description in connection with the drawings.

BRIEF DESCRIPTION OF THE DRAWINGS

FIG. 1 illustrates a preferred embodiment of the inflatable introducer of the present invention.

FIG. 2 illustrates an alternative pneumatic valve useable with the inflatable introducer.

FIG. 3 illustrates a representative type tube clamp that may be used with the inflatable introducer.

FIG. 4 illustrates the inflatable introducer of FIG. 1 in its noninflated condition positioned within a conventional nasal catheter.

FIG. 5 illustrates the inflatable introducer of FIG. 1 positioned within a preferred nasakl catheter and inflated.

FIG. 6 illustrates the inflatable introducer installed within an endotracheal tube in its noninflated condition and packaged within a sealed, sterilized pouch.

DESCRIPTION OF THE INVENTION

Referring to FIG. 1, the introducer 11 of the invention includes a hollow, cylindrical tube 12 of flexible material, such as rubber, polyvinyl chloride or other medically approved tubing, having an open proximal end 13 and an open distal end or tip 14. A hollow, cylindrically shaped sheath 15 of relatively thin material has a closed, soft and rounded tip 16 and an end portion 17 securely attached and sealed to the outside cylindrical surface of tube 12 at position 18. An airtight seal exists between the inside of sheath 15 and the outside cylindrical surface of tube 12. Approximately one-third of the length of sheath 15 extends beyond the open distal end or tip 14 of tube 12. Approximately two-thirds of the length of sheath 15 overlays the distal end portion of tube 12, as shown. The diameter of sheath 15 is somewhat larger than the outside diameter of tube 12.

The length of tube 12 is determined by the length of the catheter or endotracheal tube for which it is to be used, and the diameter of tube 12, as well as the diameter of sheath 15, is less than the inside diameter of the catheter.

Sheath 15 may be composed of polyisoprene, latex rubber, polyvinyl chloride or suitable medically approved material. Sheath 15 is designed to be inflated by air under pressure supplied through hollow tube 12, as described hereinafter.

The open proximal end 13 of tube 12 is provided with a manually controllable valve means, such as a stopcock 21. Stopcock 21 has a hollow, open proximal end 22, shaped as a connector fitting, to receive a conventional medical syringe. The connector fitting may be of the conventional "Luer" female type. The hollow, open distal end 23 of stopcock 21 is tapered and fitted within the open proximal end 13 of tube 12. Stopcock 21 includes a vertical shaft extending perpendicularly through the valve between the open proximal and distal ends 22 and 23. The vertical shaft is attached to handle 24 to enable the vertical shaft to be rotated above a vertical axis a—a. Stopcock 21 is in its open position when handle 24 is aligned in the direction shown in FIG. 1.

Stopcock 21 is representative of one of several types of valve means that may be attached to the open proximal end 13 of tube 12. An alternative valve 26 is shown in FIG. 2. Valve 26 is of the "one-way" type having a tapered, hollow, open proximal end 27, a tapered, open distal end 28, and an internal, resilient plunger or ball that normally closes the passage between the open proximal and distal ends 27 and 28. The conventional medical syringe of the piston and cylinder type is designed to attach directly over the open proximal end 27 and press against the internal, resilient plunger to open the valve. Air under pressure from the syringe then passes through valve 26 into hollow tube 12. Upon detachment of the syringe, the internal resilient plunger returns to its normally closed position, thereby sealing the passage between open proximal and distal ends 27 and 28 and closing the end of tube 12.

FIG. 3 illustrates a conventional spring-type hose or tube clamp 31 designed to slide along and around a hollow, pliable tube. Shown in its open position in FIG. 3, clamp 31 is closed by pressing the top leaf spring element 32 toward the bottom element 33, thereby squeezing tube 12 between the two jaws 34 and 35. Clamp 31 is held in its closed position by latch 36 when the tip 37 of leaf spring element 32 is forced to pass below latch 36. Tube 12 is thereby closed and remains sealed until the latch 36 releases tip 37.

FIG. 4 illustrates the inflatable introducer 11 of the present invention installed within a conventional nasal catheter 41. Catheter 41 includes a flared, open proximal end 42 and a beveled, open distal end 43. Introducer 11 is placed within catheter 41 such that the closed, smooth and rounded tip 16 of sheath 15 protrudes beyond the open distal end 43. The open distal end or tip 14 of tube 12 remains inside of the open distal end 43 of catheter 41, as shown. To aid the placement of the closed, smooth and rounded tip 16 in the correct position, the rounded tip 16 may be marked by a band 45 to be aligned with the distal end 43 of catheter 41.

Cylindrical sheath 15 is in its noninflated condition when inserted into and through catheter 41 with approximately two-thirds of its upper length remaining inside the distal end portion of catheter 41, as shown. Stopcock 21, attached to the open proximal end 13 of tube 12, is situated outside the open proximal end 42 of catheter 41 and is in its open position. The assembly of catheter, inflatable introducer with sheath, and valve means, as shown in FIG. 4, is in condition for inflation of sheath 15.

FIG. 5 illustrates the inflatable introducer 11 installed in a preferred form of nasal catheter 51 and in its inflated condition. Catheter 51 has a flared, open proximal end 52 and a blunt or square open distal end 53. Closed, smooth and rounded tip 16 of sheath 15, protruding beyond the open, square distal end 53, is inflated to a diameter equal to or slightly larger than the outer diameter of catheter 51, as shown. The square, distal end or tip 53 provides a shoulder against which inflated tip 16 of sheath 15 may bear as catheter 51 is intubated.

Approximately, two-thirds of the length of sheath 15, situated within the distal end portion of catheter 51, is also inflated to embrace and contact the inner cylindrical wall portion of the distal end of catheter 51. The physical contact between the expanded two-thirds portion of sheath 15 with the inner cylindrical wall of catheter 51 anchors and holds inflatable sheath 15 against any sliding movement as catheter 51 is intubated. Distal tip 14 of hollow tube 12 remains inside the distal end of catheter 53 in the inflated condition of sheath 15 as a precaution against any likelihood of rupture of sheath 15 by distal tip 14.

Stopcock 21, attached to the proximal end 13 of tube 12, is shown in its closed position, thereby closing and sealing tube 12. Sheath 15 is maintained in its inflated condition as catheter 51 with closed, smooth and rounded tip 16 is intubated into the passageway of a patient. Following intubation, stopcock 21 is opened by turning handle 24 to the position as shown in FIG. 1 and FIG. 4 to release the air pressure within tube 12 and sheath 13. Introducer 11 is then withdrawn from catheter 51.

FIG. 6 illustrates the inflatable introducer 11 of the present invention installed within a flexible endotracheal tube 61 of the cuff type and sealed within a tough, flexible, gas-permeable envelope 71. Endotracheal tube 61 is provided with open proximal and distal ends 62 and 63. Round distal tip 16 of sheath 15 protrudes beyond the open distal end of endotracheal tube 61 and the open proximal end of tube 12 of introducer 11 extends outside of proximal end 62.

Endotracheal tube 61 includes a thin, cylindrical cuff 64 affixed to the outer cylindrical portion of tube 61 near its open distal end 63. The interior of cuff 64 is coupled to a small, flexible pilot tube 65, a portion of which is embedded within the wall of endotracheal tube 61, and through a conventional pilot balloon 66 to an inflation valve connector 67.

Envelope 71 is provided with a rectangular rear surface 72 and a transparent overlay or front surface 73. Envelope 71 is sealed, as indicated by lines 74, and a flap 75 is provided which enables front surface 73 to be peeled away, thereby rupturing the seals and providing easy access to the appliance.

Stopcock 21, attached to the open proximal end 13 of tube 12, is in the open position, as shown by the position of handle 24. In this position, tube 12 is open and the assembled appliance within its packaged and sealed enveloped may be sterilized by the conventional ethylene oxide process of gas sterilization or by any other medically acceptable radiation process.

The invention provides an improved procedure for the intubation of catheters and endotracheal tubes by providing a smooth, soft, rounded and pliable guiding tip for entering and enlarging the passageway to be intubated. Injury and trauma to the patient is reduced. The inflatable sheath of the introducer is readily inflated after rupturing the seals of the sterilized package, while the catheter and introducer remain completely inside the package. The manually controllable valve is available for easy access to physician to facilitate inflation and closure. Following removal of the assembled and inflated appliance, the smooth, soft and rounded tip may be lubricated, by the physician, along with the outer cylindrical surface of the catheter and the appliance is prepared for intubation. Following intubation, the valve is opened to release air pressure and deflate the sheath. The introducer with sheath is then withdrawn and discarded.

Since many changes can be made in the above-described apparatus and many different embodiments of this invention could be made without departing from the scope thereof, it is intended that all matter contained in the above description or shown in the accompanying drawing shall be interpreted as illustrative and not in a limiting sense.

I claim:

1. A soft, inflatable introducer adapted to be inserted into a hollow, cylindrical nasal catheter having open proximal and distal ends, the introducer being positioned and inflated to aid the intubation of the nasal catheter into the nasopharyngeal passageway of a patient, and being deflated and withdrawn following intubation, comprising in combination:
    (a) a long, hollow, pliable tube having open proximal and distal ends, said hollow, pliable tube having an external diameter less than the inside diameter of the hollow nasal catheter with which it is to be used, and having a length approximately equal to the length of the hollow nasal catheter;
    (b) a cylindrical, elongated, inflatable sheath surrounding and enclosing the distal end portion and the open distal tip of said hollow, pliable tube, said inflatable sheath being composed of thin, soft and pliable material and having a sealed, smooth, rounded tip portion; said sheath being elongated and cylindrical in shape in its noninflated condition and the smooth, rounded tip portion being spaced apart from the open distal tip of said hollow, pliable tube approximately one-third of the length of the sheath when in its noninflated condition, the end portion of said cylindrical, inflatable sheath opposite the smooth, rounded tip portion being securely attached to the outside cylindrical surface of said hollow, pliable tube for forming an airtight seal between the inside of said inflatable sheath and the distal end portion of said hollow, pliable tube, the outer diameter of said thin, cylindrical, elongated sheath being larger than the external diameter of said long, hollow, pliable tube and being less than the inside diameter of the hollow nasal catheter; said cylindrical sheath and the distal end portion of said hollow, pliable tube being adapted for insertion into the hollow nasal catheter with the smooth, rounded tip portion of said inflatable sheath protruding beyond the open distal end of the hollow nasal catheter, the open proximal end portion of said hollow, pliable tube being adapted for receiving air of sufficient pressure to expand said cylindrical, inflatable sheath situated within the distal end portion of the hollow nasal catheter to a diameter at least as large as the inside diameter of the hollow nasal catheter to provide physical contact between the outer cylindrical surface of said thin, elongated sheath and the inner cylindrical surface of the distal end portion of the hollow nasal catheter, the expansion of said cylindrical inflatable sheath by air under pressure causing the smooth, rounded tip portion protruding beyond the open distal end of the hollow nasal catheter to expand to a diameter larger than the inside diameter of the hollow catheter to a diameter approximately equal to the outside diameter of the hollow nasal catheter; and
    (c) means associated with the open proximal end portion of said hollow, pliable tube for closing the open proximal end portion of said hollow, pliable tube after said inflatable sheath has been inflated to hold and maintain said sheath in its expanded condition to prevent sliding of said cylindrical, elongated sheath relative to the hollow nasal catheter as the catheter is being intubated, the inflated smooth, rounded tip portion of said inflatable introducer providing a soft, pliable, air-filled cushion ahead of the distal end of the hollow nasal catheter for opening the nasopharyngeal passageway of the patient through which the hollow nasal catheter is to be intubated.

2. The improved medical apparatus for intubating a passageway of a patient, comprising in combination:
    (a) a hollow, cylindrical catheter composed of soft, pliable material and having open proximal and distal ends;
    (b) a long, hollow tube of pliable material situated within said hollow, cylindrical catheter, said long, hollow tube having open proximal and distal ends, the open proximal end of said hollow tube extending outside the open proximal end of said catheter and the open distal end of said hollow tube terminating within said catheter near its distal end, said hollow tube having an external diameter less than the inside diameter of said catheter;
    (c) a cylindrical, elongated, inflatable sheath composed of thin, soft and pliable material surrounding and enclosing the distal end portion and the open distal tip of said hollow, pliable tube, said inflatable sheath having a closed, smooth, rounded distal tip portion, an open proximal end portion and a central, cylindrical portion situated between the distal tip portion and the open proximal end portion; the smooth rounded distal tip portion being spaced apart from the open distal tip of said hollow tube and protruding beyond the open distal end of said catheter, the open proximal end portion of said inflatable sheath being securely attached to the outside cylindrical surface of said hollow tube for forming an airtight seal between the inside of said inflatable sheath and the distal end portion of said hollow tube, the central, cylindrical portion of said inflatable sheath being situated within the distal end portion of said catheter and having a diameter larger than the external diameter of said hollow tube and less than the inside diameter of said catheter, the open proximal end of said hollow tube extending outside the open proximal end of said catheter being adapted for coupling to a source of air of sufficient pressure to expand the central, cylindrical portion of said inflatable sheath to a diameter at least as large as the inside diameter of said catheter to provide physical contact between the outer cylindrical surface of the central, cylindrical portion of said inflatable sheath and the inner cylindrical surface of the distal end portion of said catheter, the expansion of the central, cylindrical portion of said inflatable sheath by air under pressure causing the smooth, rounded distal tip portion protruding beyond the open distal end of said catheter to expand to a diameter larger than the inside diameter of said catheter to a diameter approximately equal to the outside diameter of said catheter; and (d) means associated with the open proximal end portion of said hollow, pliable tube for closing and sealing the open proximal end portion after said inflatable sheath has been inflated for maintaining physical contact between the outer cylindrical surface of the central, cylindrical portion with the inner cylindrical surface of the distal end portion of said catheter to prevent sliding of said inflatable sheath relative to said catheter as said catheter is being intubated, the inflated, smooth, rounded tip portion of said inflatable sheath providing a soft, pliable, air-filled cushion ahead of the distal end of said catheter for opening the passageway of the patient through which said catheter is to be intubated, said means associated with the open proximal end portion of said hollow, pliable tube including means for opening the open proximal end of said hollow, pliable tube after intubation of said catheter to deflate said inflatable sheath, thereby allowing said hollow, pliable tube and inflatable sheath to be withdrawn from said catheter.

* * * * *